US006221033B1

(12) United States Patent
Blanchard et al.

(10) Patent No.: US 6,221,033 B1
(45) **Date of Patent: *Apr. 24, 2001**

(54) CONTINUOUS PASSIVE MOTION DEVICE THAT ACCELERATES THROUGH THE NON-WORKING RANGE OF MOTION

(75) Inventors: Frederick W. Blanchard, Portage, MI (US); Stephen L. Brown, Chattanooga, TN (US); Dwayne Hofstatter, Woodstock, GA (US); D. Chris Linville, Hixson, TN (US); Jeffrey K. Pohl, Chattanooga, TN (US); James R. Vetter, Jr., Soddy Daisy, TN (US)

(73) Assignee: Chattanooga Group, Inc., Hixson, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/437,172

(22) Filed: Nov. 9, 1999

(51) Int. Cl.[7] .......... A61M 1/00
(52) U.S. Cl. .......... 601/34; 601/33; 601/23
(58) Field of Search .......... 601/23–35; 606/240–244

(56) References Cited

U.S. PATENT DOCUMENTS

| | | | |
|---|---|---|---|
| 4,323,060 * | 4/1982 | Pecheux | 601/34 |
| 4,487,199 | 12/1984 | Saringer . | |
| 4,492,222 | 1/1985 | Hajianpour . | |
| 4,509,509 * | 4/1985 | Bouvet et al. | 601/34 |
| 4,520,827 | 6/1985 | Wright et al. . | |
| 4,549,534 | 10/1985 | Zagorski et al. . | |
| 4,558,692 | 12/1985 | Greiner . | |
| 4,566,440 | 1/1986 | Berner et al. . | |
| 4,602,618 | 7/1986 | Berze . | |
| 4,603,687 | 8/1986 | Greenwood . | |
| 4,621,620 * | 11/1986 | Anderson | 601/34 |
| 4,637,379 | 1/1987 | Saringer . | |
| 4,665,899 | 5/1987 | Farris et al. . | |
| 4,671,257 | 6/1987 | Kaiser et al. . | |
| 4,798,197 | 1/1989 | Nippoldt et al. . | |
| 4,807,601 | 2/1989 | Wright . | |
| 4,825,852 | 5/1989 | Genovese et al. . | |
| 4,834,073 | 5/1989 | Bledsoe et al. . | |
| 4,930,497 | 6/1990 | Saringer . | |
| 5,228,432 | 7/1993 | Kaiser et al. . | |
| 5,239,987 | 8/1993 | Kaiser et al. . | |
| 5,252,102 | 10/1993 | Singer et al. . | |
| 5,255,188 | 10/1993 | Telepko . | |
| 5,273,520 * | 12/1993 | Rebmann | 601/34 |
| 5,277,681 * | 1/1994 | Holt | 482/112 |
| 5,280,783 | 1/1994 | Focht et al. . | |
| 5,303,716 | 4/1994 | Mason et al. . | |
| 5,399,147 | 3/1995 | Kaiser . | |
| 5,452,205 | 9/1995 | Telepko . | |
| 5,509,894 | 4/1996 | Mason et al. . | |
| 5,682,327 | 10/1997 | Telepko . | |

OTHER PUBLICATIONS

Advertisement for Breg Flex–Mate K500, 1997.

* cited by examiner

*Primary Examiner*—Justine R. Yu
(74) *Attorney, Agent, or Firm*—Chambliss, Bahner & Stophel, P.C.

(57) ABSTRACT

A therapeutic device which may be used in providing physical therapy for a patient's knee by moving the patient's leg through a plurality of cycles of motion in a treatment session. The device includes a "Fast Back" range of motion feature that permits the machine to be operated at more than one speed or rate per cycle, wherein the patient's knee may pass through a critical or working range of motion at a first rate, and through a non-critical or non-working range of motion at a second rate, so as to increase the portion of time of a treatment session that is spent in the working of the range of motion, as compared to conventional CPM machines. The preferred embodiment of the invention also has "soft turns" capability, wherein the carriage holding the patient's leg is decelerated, at a controlled rate over a controlled distance, from the operational speed to zero, as the carriage approaches an extension or flexion limit, and wherein the carriage is accelerated in the same fashion as the carriage moves away from the extension or flexion limit.

19 Claims, 5 Drawing Sheets

CONTINUOUS PASSIVE MOTION DEVICE THAT ACCELERATES THROUGH THE NON-WORKING RANGE OF MOTION

FIELD OF THE INVENTION

The present invention relates generally to medical rehabilitation devices, and more particularly to a device which may be used to flex the knee joint of a patient as part of a therapeutic or rehabilitative program.

BACKGROUND OF THE INVENTION

Knee injuries are an unfortunate byproduct of today's emphasis on sports and physical fitness; however, effective surgical techniques have been developed to repair injuries such as to the anterior cruciate ligament (ACL) and other components of the knee. In addition, many members of our aging population are candidates for total knee replacement surgery because of disease and/or injury. All of these surgical procedures must be followed by a period of rehabilitation in order for recovery to be complete. Furthermore, some injuries to the knee may not require surgery but instead may require an extensive rehabilitation period. Such rehabilitation generally requires that the knee be flexed and the leg be extended such as occurs in normal walking; however, it is frequently undesirable for a recovering patient to bear weight on his leg while rehabilitating his knee. In addition, when a knee has suffered a trauma or other injury, or after surgery, a person often lacks the necessary muscle control, strength or will to flex his knee and straighten his leg. Consequently, there is a need for a rehabilitation device that can be used to mobilize the joint over period of time as a part of the orthopedic care which follows an injury, illness or surgical procedure.

The therapeutic use of an external force to flex and extend the limb to induce motion is referred to as passive motion. The application of continuous passive motion to a joint following a period of immobilization, injury, surgery or the like, has been shown to reduce post-operative pain, decrease the number of adhesions, decrease the amount of atrophy experienced by the surrounding and supporting muscle, promote the speed of recovery, improve the range of motion in a much shorter time, and reduce the risk of deep vein thrombosis and post-traumatic osteopenia. Depending on the nature and severity of the knee injury or the nature and extent of the surgical procedure performed, therapeutic treatment sessions involving continuous passive motion may be carried out on a daily basis for several days or several weeks.

The concept of a therapeutic use of passive and continuous motion is not new, as evidenced by a number of known devices that are designed to impose continuous passive motion on the limb and joint of a patient for such purpose. For example, U.S. Pat. No. 4,492,222 of Hajianpour describes a knee exerciser comprised of a leg support that is hinged at one end to a thigh support and is fixed at its other end to a motor assembly. The other end of the thigh support is pivotally attached to a frame, and the motor assembly is also pivotally attached to the frame. A screw that is threaded into a tubular portion of the leg support is rotated by the motor to drive the device. The Hajianpour device also includes an up/down counter that is arranged to count revolutions of the motor drive shaft via a magnetic sensor. When the count of the counter reaches either the flexion or extension limits, the direction of rotation of the motor is changed. U.S. Pat. No. 4,558,692 of Greiner describes a motor driven leg exerciser having an adjustable leg support, a movable footrest, a motor, and controls for the user or therapist. In operation, the motor drives a chain driven rod back and forth in an arc to move the leg support. As the rod reaches each end of its arc, it activates a directional switch which in turn stops the motor, causes the device to pause for a predetermined period of time, and reverses the direction of the rod. The arcuate movement of the rod causes the leg support to move the patient's leg from an extended position to a bent position.

As the use of therapeutic continuous passive motion (CPM) machines has increased, so too have the number of developments and improvements in the related technology. For example, U.S. Pat. No. 4,798,197 of Nippoldt et al. and U.S. Pat. No. 4,558,692 of Greiner describe various safety features which, upon the occurrence of any of several conditions, will cause the carriage holding the leg to stop and reverse direction; U.S. Pat. No. 4,825,852 of Genovese et al. describes hinges between the upper and lower members of the leg support which are designed to better mimic the motion of the knee joint and thereby increase patient comfort; U.S. Pat. No. 5,255,188 and No. 5,452,205, both of Telepko, describe a universal controller for a CPM device which includes a clock and a liquid crystal display for displaying the accumulated running time for an exercise session; U.S. Pat. No. 5,682,327 of Telepko describes a direct drive CPM device which maintains an approximately constant angular velocity at the knee so as to increase the comfort level of the patient; and U.S. Pat. No. 4,665,899 of Farris et al. describes a CPM device having control means which allow the user or a therapist to change the degree of extension and flexion of the leg, and also having a repetition counter that can count and display the number of flexion repetitions completed. Furthermore, U.S. Pat. No. 4,566,440 of Berner, et al. and U.S. Pat. No. 5,682,327 of Telepko describe continuous passive motion devices which pivot the patient's leg about a virtual axis that is coincident with the hip pivot axis. This helps to avoid placing unnecessary strain on the patients leg or hip joint, and increases the comfort of the patient as treatment is carried out. Finally, U.S. Pat. No. 5,682,327 of Telepko describes a "warm-up" mode of operation by which the range of motion of the device is automatically and gradually increased over a preset period of time at the beginning of a treatment session. U.S. Pat. No. 4,825,852 of Genovese et al. describes a similar "warm-up" feature by which the programmed force and range of motion is automatically reduced somewhat when exercise is restarted after a rest period.

Despite these improvements in CPM technology, conventional CPM devices suffer from several disadvantages. Among these is the fact that conventional CPM machines generally operate at a constant speed throughout a programmed range of motion. However, the inventors of the present invention have learned that therapeutic benefits may be obtained if a greater portion of the treatment time is spent in flexion (or extension) within a critical portion of the range of motion near the flexion (or extension) limit. Therefore, it would also be desirable if a continuous passive motion device could be developed that would concentrate the time spent in a treatment session in flexing the patient's knee or extending his leg through the critical or working portion of the range of motion. It would also be desirable if such a device could be developed that would be relatively simple for a patient to operate and therefore, more likely to be properly used.

Another disadvantage of the constant speed CPM machines is that the carriage holding the patient's leg is rapidly decelerated from the operational speed of the carriage to zero as the carriage reaches its operational extension or flexion limit, and rapidly accelerated from zero to the operational speed in the opposite direction as the carriage moves away from the limit. Such sudden speed and direction changes are uncomfortable for the patient and may impose undesirable stresses on his knee and leg. It would be desirable therefore, if a CPM device could be developed which would allow the carriage to make "soft turns" when changing directions.

ADVANTAGES OF THE INVENTION

Accordingly, the invention described and claimed herein provides among its advantages that a patient or therapist may adjust the speed or rate at which the carriage of a continuous passive motion device moves the patient's leg through one or more portions of the operational range of motion of the device, thereby enabling the patient to spend an increased portion of the treatment time in the critical portion of the range of motion, as compared to conventional CPM machines. Another advantage of a preferred embodiment of the invention is its "soft turns" capability, wherein the carriage holding the patient's leg is decelerated, at a controlled rate over a controlled distance, from the operational speed to zero, as the carriage approaches the extension or flexion limit, and wherein the carriage is accelerated in the same fashion as the carriage moves away from the extension or flexion limit.

Other advantages and features of this invention will become apparent from an examination of the drawings and the ensuing description.

EXPLANATION OF TECHNICAL TERMS

As used herein, the term range of motion refers to a range of angular motion between the lower leg support and the upper leg support of the invention. The term range of motion may also refer to the range of angular motion that is or may be imposed on a patient's knee by the invention, as measured by the change in the angle between the tibia and the femur of the patient's leg.

As used herein, the term flexion refers to that portion of a range of motion in which the angle between the lower leg support and the upper leg support of the invention, or the angle between the tibia and the femur of the patient's leg, is decreasing.

As used herein, the term flexion phase refers to that portion or phase of the operation of the invention during which flexion occurs.

As used herein, the term extension refers to that portion of a range of motion in which the angle between the lower leg support and the upper leg support of the invention, or the angle between the tibia and the femur of the patient's leg, is increasing.

As used herein, the term extension phase refers to that portion or phase of the operation of the invention during which extension occurs.

As used herein, the term flexion limit refers to a limit that may be imposed during flexion on the angle between the lower leg support and the upper leg support of the invention, or on the angle between the tibia and the femur of the patient's leg. The term flexion limit also refers to a point along the axis of the frame of the preferred embodiment of the invention to which, but not beyond which, the driver may be moved by operation of the motor during a flexion phase. When the driver reaches the flexion limit, the direction of motion of the driver along the axis of the frame will change and extension will begin.

As used herein, the term extension limit refers to a limit to extension that may be imposed on the angle between the lower leg support and the upper leg support of the invention, or on the angle between the tibia and the femur of the patients leg. The term extension limit also refers to a point along the axis of the frame of the preferred embodiment of the invention to which, but not beyond which, the driver may be moved by operation of the motor during an extension phase. When the driver reaches an extension limit, the direction of motion of the driver along the axis of the frame will change and flexion will begin. An extension limit of greater than 180° may be referred to as hyperextension.

As used herein, the term limit may refer to either an extension limit or a flexion limit, depending on the context.

As used herein, the term flexion angle refers to the angle between the lower leg support and the upper leg support of the invention at a point during a flexion phase or at a particular flexion limit.

As used herein, the term extension angle refers to the angle between the lower leg support and the upper leg support of the invention at a point during an extension phase or at a particular extension limit.

As used herein, the term cycle refers to a continuous operation of the invention either from a flexion limit to an extension limit and back to a flexion limit, or from an extension limit to a flexion limit and back to an extension limit. The term cycle also refers to the movement of a patient's leg through a single flexion phase and a single extension phase.

As used herein, the term treatment time refers to the time during which the invention is operated continuously to move the patient's leg through a plurality of cycles, even though such operation may include one or more pauses in the motion imparted to the patient's leg.

As used herein, the term treatment session refers to a use of the invention for a treatment time.

As used herein, the term operational flexion limit refers to a flexion limit that is established for a selected range of motion. The operational flexion limit may be changed during a treatment session.

As used herein, the term operational extension limit refers to an extension limit that is established for a selected range of motion. The operational extension limit may be changed during a treatment session.

As used herein, the terms speed or rate of operation refer to the rate of change of the angle between the upper leg support and the lower leg support, as such supports pivot at the connection therebetween, per unit of time. As used herein in connection with the preferred embodiment, the terms speed or rate of operation may also refer to the rate at which the driver moves along the axis of the frame per unit of time, although such rate is typically expressed in terms of the rate of change of the angle between the upper leg support and the lower leg support.

As used herein, the term critical range of motion or working range of motion refers to that portion of the range of motion (typically, but not limited to, that portion of the range of motion near a flexion limit during the flexion phase and/or that portion of the range of motion near an extension limit during the extension phase) where therapeutic benefit is most likely to be obtained as a result of flexion or extension movements. As used herein, the critical range of motion or working range of motion refers to that portion of the range of motion between an intermediate flexion limit and the operational limit in the flexion phase or between an intermediate limit and the operational extension limit in the extension phase.

As used herein, the term non-critical range of motion or non-working range of motion refers to that portion of the range of motion outside of the critical or working range of motion.

SUMMARY OF THE INVENTION

The invention comprises a therapeutic device for use in providing physical therapy for a patient's knee by moving the patient's leg through a plurality of cycles of motion in a treatment session.

The device includes a "Fast Back" range of motion feature that permits the machine to be operated at more than one speed or rate per cycle, wherein the patient's knee may pass through a critical or working range of motion at a first rate, and through a non-critical or non-working range of motion at a second rate, so as to increase the portion of time of a treatment session that is spent in the working range of motion.

The therapeutic device includes an elongated frame having an axis, a lower leg support which is adapted to support the lower leg of the patient, and an upper leg support which is adapted to support the upper leg of the patient. Each of the lower leg support and the upper leg support has a first end and a second end, and the first end of the upper leg support is pivotally connected to the first end of the lower leg support. The frame, lower leg support and upper leg support are interconnected in a manner such that both the tibia and the femur of the patient are generally coplanar with the axis of the frame. The device also includes means for repeatedly pivoting the lower leg support and the upper leg support at the connection therebetween so as to move the patients leg through a plurality of cycles of motion, each of which imposes a range of motion on the patient's leg comprising a flexion phase, in which the angle between the lower leg support and the upper leg support is decreasing, and an extension phase, in which the angle between the lower leg support and the upper leg support is increasing. The device also includes means for setting a desired range of motion including an operational extension limit and an operational flexion limit. The operational extension limit corresponds to an operational extension angle between the upper leg support and the lower leg support to which the upper and lower leg supports may be pivoted during the extension phase of a cycle, and the operational flexion limit corresponds to an operational flexion angle between the upper leg support and the lower leg support to which the upper and lower leg supports may be pivoted during the flexion phase of a cycle. The device also includes means for setting an intermediate limit the range of motion. The intermediate limit corresponds to a critical angle between the upper leg support and the lower leg support. The intermediate limit may be set to affect the rate of operation during an extension phase or an extension limit. If set to affect the rate of operation during a flexion phase, the intermediate limit will correspond to a critical flexion angle between the upper leg support and the lower leg support that is greater than the operational flexion angle. If set as to affect the rate of operation during an extension phase, the intermediate limit will correspond to a critical extension angle that is less than the operational extension angle. The device also includes means for setting a first and a second rate of operation at which the upper leg support and the lower leg support may be pivoted at the connection therebetween. The device also includes means for changing the rate at which the lower leg support and the upper leg support may be pivoted from the first rate to the second rate at the intermediate limit. If set to correspond to a critical extension angle, the rate of operation will change from the first rate to the second rate during the extension phase. If set to correspond to critical flexion angle, the rate of operation will change from the first rate to the second rate during the flexion phase. The device further includes means for changing the rate of operation from the second rate to the first rate at the operational limit. If the intermediate rate is set to correspond to a critical extension angle, the rate of operation will change from the second rate to the first at the operational extension limit. If the intermediate rate is set to correspond to critical flexion angle, the rate of operation will change from the second rate to the first rate at the operational flexion limit.

Furthermore, the invention provides a method for providing physical therapy for a patient's knee by moving the patient's leg through a plurality of cycles of motion in a manner which allows the patient's knee to experience an increased amount of time in the working range of motion.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to those skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
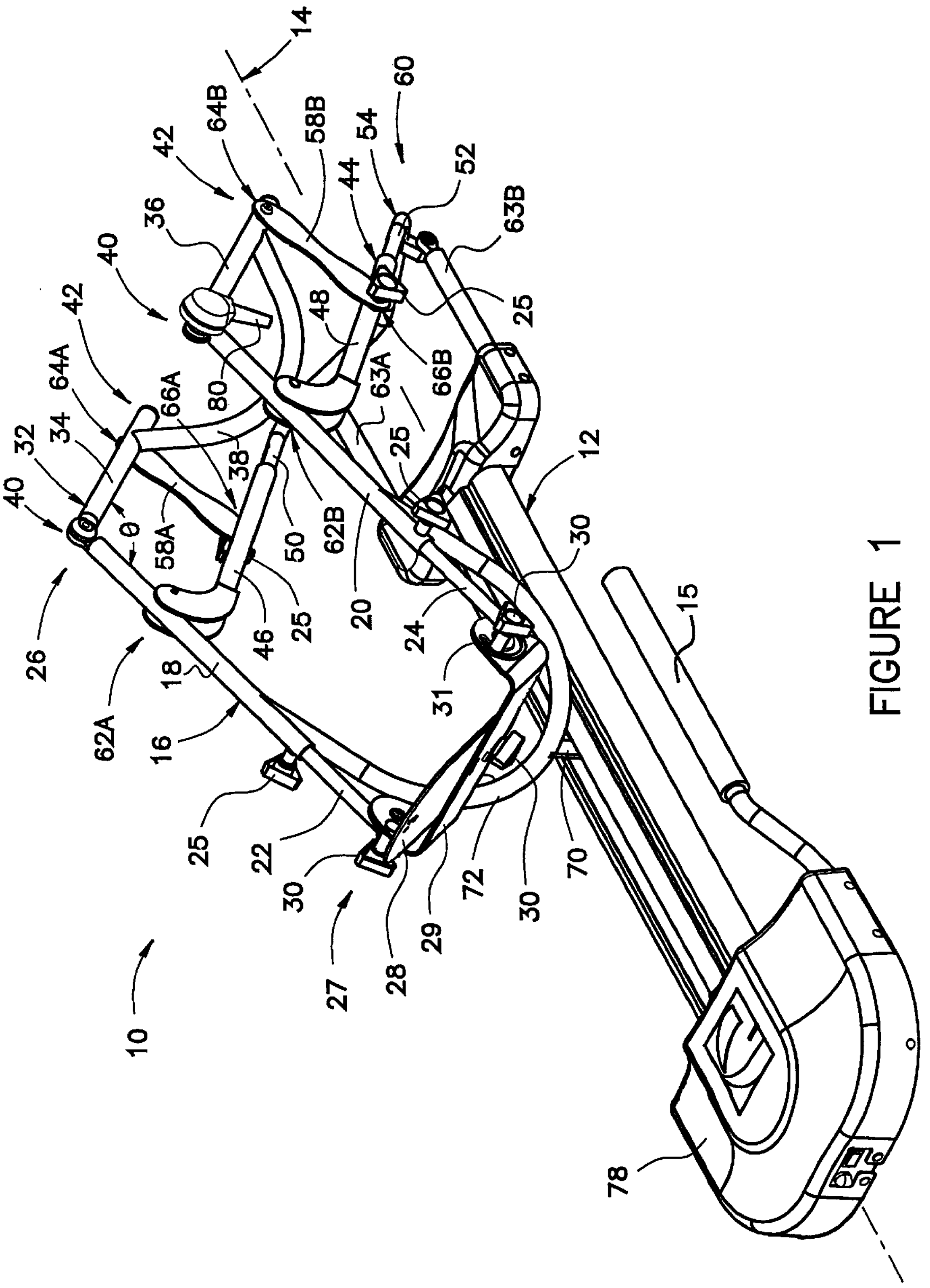
FIG. 1 is a front perspective view of the preferred embodiment of the therapeutic device.

Referring now to the drawings, preferred therapeutic device 10 operates by application of continuous passive motion to the knee joint of a patient during a treatment session that includes flexion of the knee and extension of the leg. Such motion is considered to be continuous or substantially continuous even though there will or may be pauses at the flexion and extension limits, and perhaps at other times. Device 10 may be utilized in providing a regimen of physical therapy for a patient's knee by moving the patient's leg through a plurality of cycles of motion in each of a number of treatment sessions.

Figure 2:
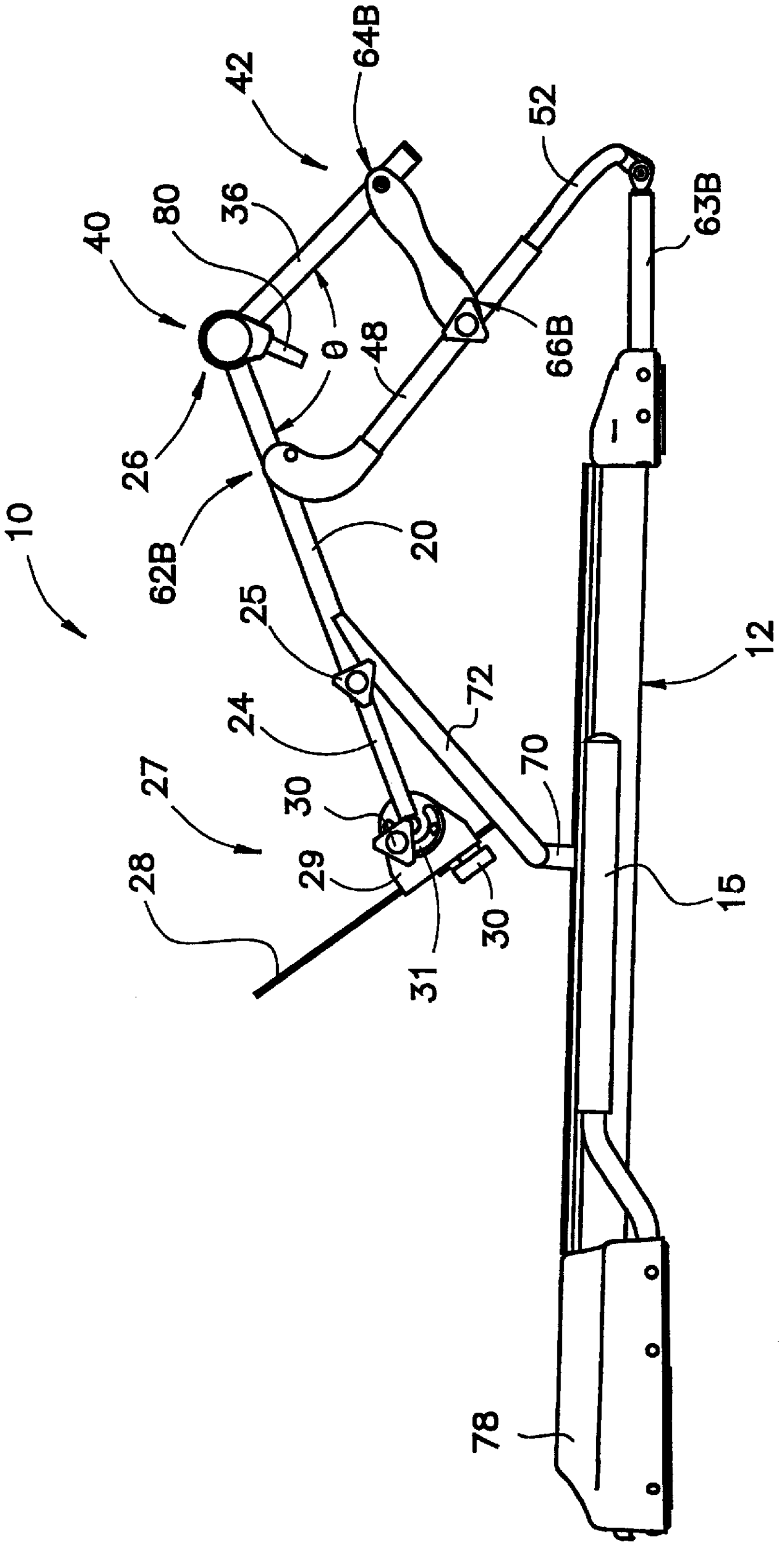
FIG. 2 is a side view of the device of FIG. 1.
Figure 3:
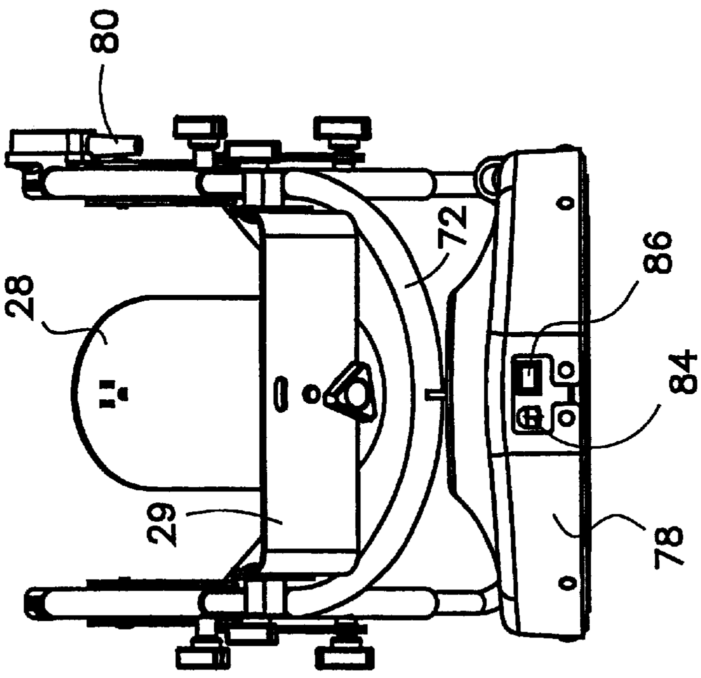
FIG. 3 is a front elevation view of the device of FIG. 1.
Figure 4:
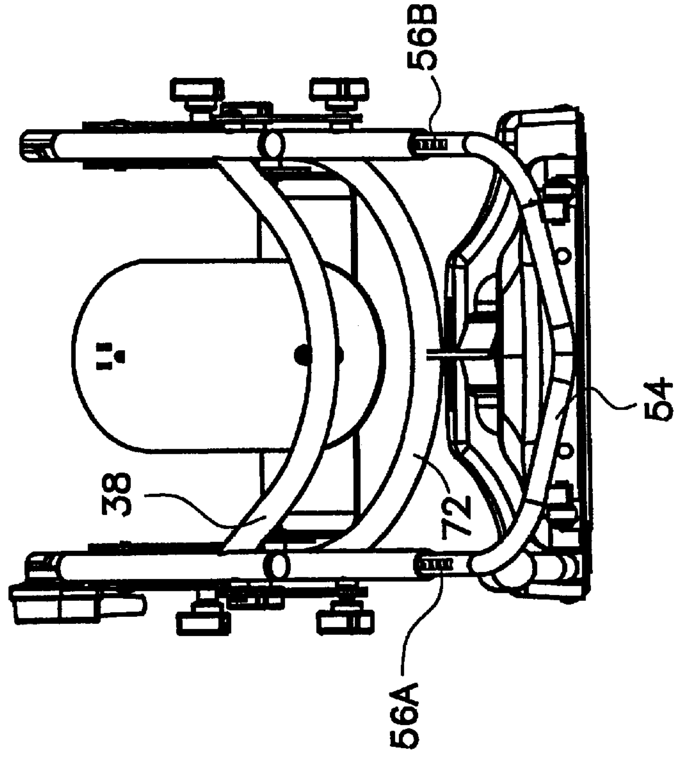
FIG. 4 is a rear elevation view of the device of FIG. 1.

Referring now to FIGS. 1 through 4, therapeutic device 10 includes elongated frame 12 having an axis 14 along its length. Preferably, the frame also includes carrying handle 15 which is located and balanced to provide easy portability of the machine. Device 10 also includes lower leg support 16 which is adapted to support the lower leg of the patient. Lower leg support 16 is preferably comprised of a pair of parallel tubular components 18 and 20 to which are attached a pair of telescoping end tubes 22 and 24, respectively. Each of the end tubes is adapted for sliding motion within the tubular component with which it is associated so as to permit adjustment of the length of the lower leg support to accommodate the lower leg length of the patient. Each of tubular components 18 and 20 is provided with a hole (not shown) through which a length adjusting bolt 25 may be placed in threaded engagement therewith. The adjusting bolt may then be advanced in the hole to bear against the surface of the end tube, and thereby to hold it securely in place. In the alternative, a length adjusting bolt 25 may be provided to engage with one of a series of holes (not shown) that are provided along the length of each of end tubes 22 and 24. By selecting the appropriate holes along the length of the end tubes for attachment to the tubular components, the length of the lower leg support may be adjusted to accommodate the lower leg length of the patient. Lower leg support 16 has a first end designated generally at 26 near the knee of the patient and a second end designated generally at 27 adjacent to the patient's foot. Preferably, foot support 28 is mounted to the lower leg support through pivotally attached end plate 29. As shown in FIGS. 1 through 3, the foot support is attached to the end plate by means of bolt 30. The end plate is provided with an arc-shaped bolt hole 31 at each end into which a pair of bolts 30, fixed to the ends of tubes 22 and 24, may be placed for pivotal attachment to the lower leg support.

Device 10 also includes an upper leg support 32 which is adapted to support the upper leg of the patient. Upper leg support 32 of preferred device 10 includes an upper portion comprised of a pair of parallel tubular components 34 and 36 and a connecting cross support member 38. The upper leg support has a first end designated generally at 40 near the knee of the patient and a second end designated generally at 42 adjacent to the patient's hip. First end 40 of upper leg support 32 is pivotally connected to first end 26 of lower leg support 16.

The upper leg support of preferred therapeutic device 10 also includes U-shaped third support 44, which is comprised of a pair of parallel tubular components 46 and 48 to which are attached a pair of telescoping end tubes 50 and 52, respectively, of U-shaped end portion 54. Each of the end tubes is adapted for sliding motion within the tubular component with which it is associated so as to permit adjustment of the length of the upper leg support to accommodate the upper leg length of the patient. Each of tubular components 46 and 48 is provided with a hole (not shown) through which a length adjusting bolt 25 may be placed in threaded engagement therewith. The adjusting bolt may then be advanced in the hole to bear against the surface of the end tube, and thereby to hold it securely in place. In the alternative, a length adjusting bolt 25 may be provided to engage with one of a series of holes (not shown) that are provided along the length of each of end tubes 50 and 52. By selecting the appropriate holes along the length of the end tubes for attachment to the tubular components, the length of the upper leg support may be adjusted to accommodate the upper leg length of the patient. Scales 56A and 56B (see FIG. 4) are provided for convenience in adjusting the length of the upper leg support. The scales correspond to upper leg lengths for patients of different sizes. A patient's upper leg, from his hip to his knee, may be measured and components 50 and 52 slid into components 46 and 48 respectively until the ends of components 50 and 52 reach the patient's measured length on scales 56A and 56B. The third support has a first end 60 and a second end 62. First end 60 is pivotally attached to extensions 63A and 63B of frame 12, and second end 62 is pivotally attached to lower leg support 16 (second end 62A is attached to tubular component 18 and second end 62B is attached to tubular component 20).

Preferred upper leg support 32 also includes a pair of linkage members 58A and 58B (sometimes referred to herein collectively as linkage). The linkage members also have a first end 64 and a second end 66. First end 64A of linkage member 58A is pivotally attached to tubular component 34 of upper leg support 32 at or near second end 42, and second end 66A of linkage member 58A is pivotally attached to tubular component 46 of third support 44 (by means of a bolt 25) at a point intermediate between first end 60 and second end 62. Similarly, first end 64B of linkage member 58B is pivotally attached to tubular component 34 of upper leg support 32 at or near second end 42, and second end 66B of linkage member 58B is pivotally attached (by means of a bolt 25) to tubular component 48 of third support 44 at a point intermediate between first end 60 and second end 62.

Figure 5:
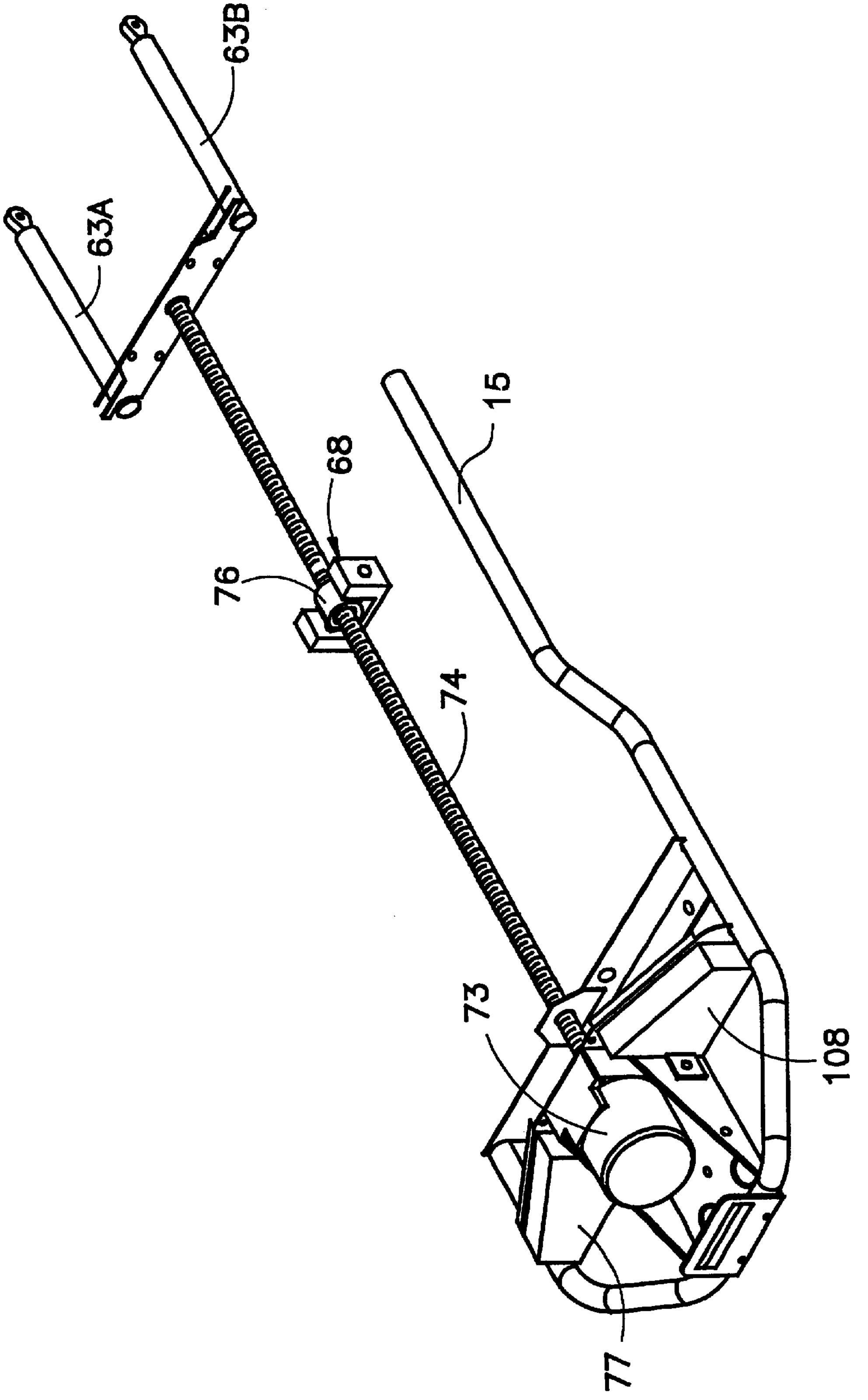
FIG. 5 is a partial front perspective view of the preferred embodiment of the invention, similar to FIG. 1 but showing details of the drive mechanism of the invention.

As has been mentioned, first end 26 of lower leg support 16 is pivotally attached to first end 40 of upper leg support 32. Device 10 is adapted to repeatedly pivot the lower leg support and the upper leg support at this connection so as to move the patient's leg through a plurality of cycles of motion, each of which imposes a range of motion on the patient's leg comprising a flexion phase in which the angle θ (see FIGS. 1 and 2) between the lower leg support and the upper leg support is decreasing, and an extension phase in which the angle θ between the lower leg support and the upper leg support is increasing. The pivotal motion of the upper and lower leg supports is preferably obtained by the movement of driver 68 (see FIG. 5), which is attached to the second end of lower leg support 16 through upright attachment 70 and U-shaped tubular stabilizer 72. Preferably, the tubular stabilizer component of the lower leg support is welded to tubular components 18 and 20 and to upright attachment 70. The driver is adapted to move in both directions along the axis 14 of the frame by operation of motor 73 (see FIG. 5). Preferably, the motor is adapted to turn externally threaded drive rod 74 which is mounted in the frame and disposed along the axis of the frame, and driver 68 includes an internally threaded nut 76 that is adapted to mate with the drive rod. As shown in FIG. 5, nut 76 is mounted on the drive rod in threaded engagement therewith, so that the driver may be moved along the axis of the frame as the drive rod is turned by the motor.

In an alternative embodiment (not shown), the drive means of the invention may include a pulley and a cord mounted thereon, which cord is adapted to be moved along the axis of the frame by operation of the motor. In such embodiment, the driver is attached to the cord and is adapted to move along the axis of the frame as the cord is moved by operation of the motor. Still another embodiment (also not shown) of the drive means may be provided by a piston which is mounted in the frame and disposed along the axis thereof. In this embodiment, the piston has a piston rod that is adapted to be moved along the axis of the frame by operation of a pump, and the driver is attached to the piston rod and is adapted to move along the axis of the frame as the piston is operated by the pump.

By lying on his back at the rear of device 10 (to the right in FIGS. 1 and 2), a patient may place his leg in the device in proper supporting manner so that his upper leg is supported by support 32 and his lower leg is supported by support 16, with his knee located generally at the junction of first end 40 of upper leg support and first end 26 of lower leg support. As is apparent from an examination of the drawings, the frame, lower leg support and upper leg support are interconnected in a manner such that both the tibia (of the lower leg) and the femur (of the upper leg) of the patient are generally coplanar with the axis of the frame. Furthermore, because of the connection of the lower leg support to the driver, as illustrated in the drawings, movement of the driver in one direction along the axis will cause extension and movement of the driver in the opposite direction along the axis will cause flexion.

The invention includes a computer controller 77 such as is known generally to those having ordinary skill in the art to which the invention relates. This controller is mounted within housing 78, and wiring (not shown) is provided from the controller through the frame and through the various tubular components to control jack 80 (see FIG. 1). A control pendant 82 (see FIG. 6) is provided with a control cord (not shown) that is adapted to be plugged into the control jack to permit a therapist and/or the patient to access the controller. The combination controller 77 and control pendant 82, connected through the control cord of the pendant and jack 80, provides means for controlling the various functions of the invention. The invention thus includes control means for setting a desired range of motion including an operational extension limit and an operational flexion limit. The operational extension limit corresponds to an operational extension angle $\theta_{oe}$ between the upper leg support and the lower leg support to which the upper and lower leg supports may be pivoted during the extension phase of a cycle. In the embodiment of the invention that is illustrated in the drawings, the operational extension limit also corresponds to a point along the axis of the frame to which the driver may be moved during the extension phase by operation of the motor to establish an operational extension angle $\theta_{oe}$. The operational flexion limit corresponds to an operational flexion angle $\theta_{of}$ between the upper leg support and the lower leg support to which the upper and lower leg supports may be pivoted during the flexion phase of a cycle. In the embodiment of the invention that is illustrated in the drawings, the operational flexion limit also corresponds to a point along the axis of the frame to which the driver may be moved by operation of the motor during the flexion phase to establish an operational flexion angle $\theta_{of}$. Furthermore, the control means (comprising the combination of controller 77 and control pendant 82) for setting a desired range of motion in the illustrated embodiment includes limit switches or other means to insure that when the driver is moved by the operation of the motor to an operational extension limit, it will reverse direction and move towards the operational flexion limit. Similarly, when the driver is moved to an operational flexion limit, it will reverse direction and move towards the operational extension limit.

The upper leg support and the lower leg support may be referred to as the carriage, and the pivoting movement of the upper leg support and the lower leg support during a flexion phase may be referred to as moving the carriage towards the flexion limit. Similarly the pivoting movement of the upper leg support and the lower leg support during an extension phase may be referred to as moving the carriage towards the extension limit.

The device includes a Fast Back range of motion feature that permits the machine to be operated at more than one speed or rate per cycle, so that the carriage supporting the patient's leg may move the knee through a critical or working range of motion at a first rate, and through the noncritical or non-working range of motion, or the remainder of the range of motion, at a second rate, in order to increase the proportion of time spent in the critical or working portion of the range of motion, as compared to conventional CPM machines.

As a part of this feature, the invention also includes control means (comprised of the combination of controller 77 and control pendant 82) for setting an intermediate limit to the range of motion. The intermediate limit corresponds to a critical angle $\theta_c$ between the upper leg support and the lower leg support, which angle will correspond, in the illustrated embodiment, to a point along the axis of the frame to which the driver may be moved by operation of the motor. The intermediate limit may be set to affect the rate of operation during a flexion phase or an extension phase, but in either event, it will represent the beginning point of the critical portion of the range of motion. If the intermediate limit is set to affect the rate of operation during a flexion phase, the intermediate limit will correspond to a critical flexion angle $\theta_{cf}$ between the upper leg support and the lower leg support that is greater than the operational flexion angle and will define the critical portion of the range of motion between the critical flexion angle $\theta_{cf}$ and the operational flexion angle $\theta_{of}$. If the intermediate limit is set to affect the rate of operation during an extension phase, the intermediate limit will correspond to a critical extension angle $\theta_{ce}$ that is less than the operational extension angle and will define the critical portion of the range of motion between the critical extension angle $\theta_{ce}$ and the operational extension angle $\theta_{oe}$.

The device also includes means (comprised of the combination of controller 77 and control pendant 82) for setting a first and a second rate at which the upper leg support and the lower leg support may be pivoted at the connection therebetween. The device further includes means (comprised of the combination of controller 77 and control pendant 82) for changing the rate at which the lower leg support and the upper leg support may be pivoted at the connection therebetween from the first rate of operation to the second rate at the intermediate limit. If the intermediate limit is set to affect the rate of operation during an extension phase, the rate of operation will change from the first rate to the second rate during the extension phase. If the intermediate limit is set to affect the rate of operation during a flexion phase, the rate of operation will change from the first rate to the second rate during the flexion phase. The device also includes means (comprised of the combination of controller 77 and control pendant 82) for changing the rate at which the lower leg support and the upper leg support may be pivoted at the connection therebetween from the second rate of operation to the first rate of operation at the operational limit. If the intermediate limit is set to affect the rate of operation during an extension phase, the rate of operation will change from the second rate to the first at the operational extension limit. If the intermediate limit is set to affect the rate of operation during a flexion phase, the rate of operation will change from the second rate to the first rate at the operational flexion limit.

The preferred embodiment of the invention further includes means (comprised of the combination of controller 77 and control pendant 82) for setting at least one trigger limit to the range of motion. The trigger limit corresponds to a trigger angle $\theta_t$ between the upper leg support and the lower leg support, which angle will correspond, in the illustrated embodiment, to a point along the axis of the frame to which the driver may be moved by operation of the motor.

The trigger limit may be set to affect the rate of operation during a flexion phase or an extension phase. If the trigger limit is set to affect the rate of operation during a flexion phase, the trigger limit will correspond to a trigger flexion angle $\theta_{tf}$ between the upper leg support and the lower leg support that is greater than the critical flexion angle. If the trigger limit is set to affect the rate of operation during an extension phase, the trigger limit will correspond to a trigger extension angle $\theta_{te}$ between the upper leg support and the lower leg support that is less than the critical extension angle. The device also includes means (comprised of the combination of controller 77 and control pendant 82) for decelerating the rate at which the lower leg support and the upper leg support may be pivoted at the connection therebetween from a first rate at the trigger limit to a second rate at the intermediate limit so as to reduce the potential for discomfort or injury to the patient as the device changes its rate of pivoting operation. If the intermediate angle is set as an extension angle, it is preferred that the trigger extension angle be approximately 5° less than the critical extension angle. If the intermediate angle is set as a flexion angle, it is preferred that the trigger flexion angle be approximately 5° greater than the critical extension angle.

Figure 6:
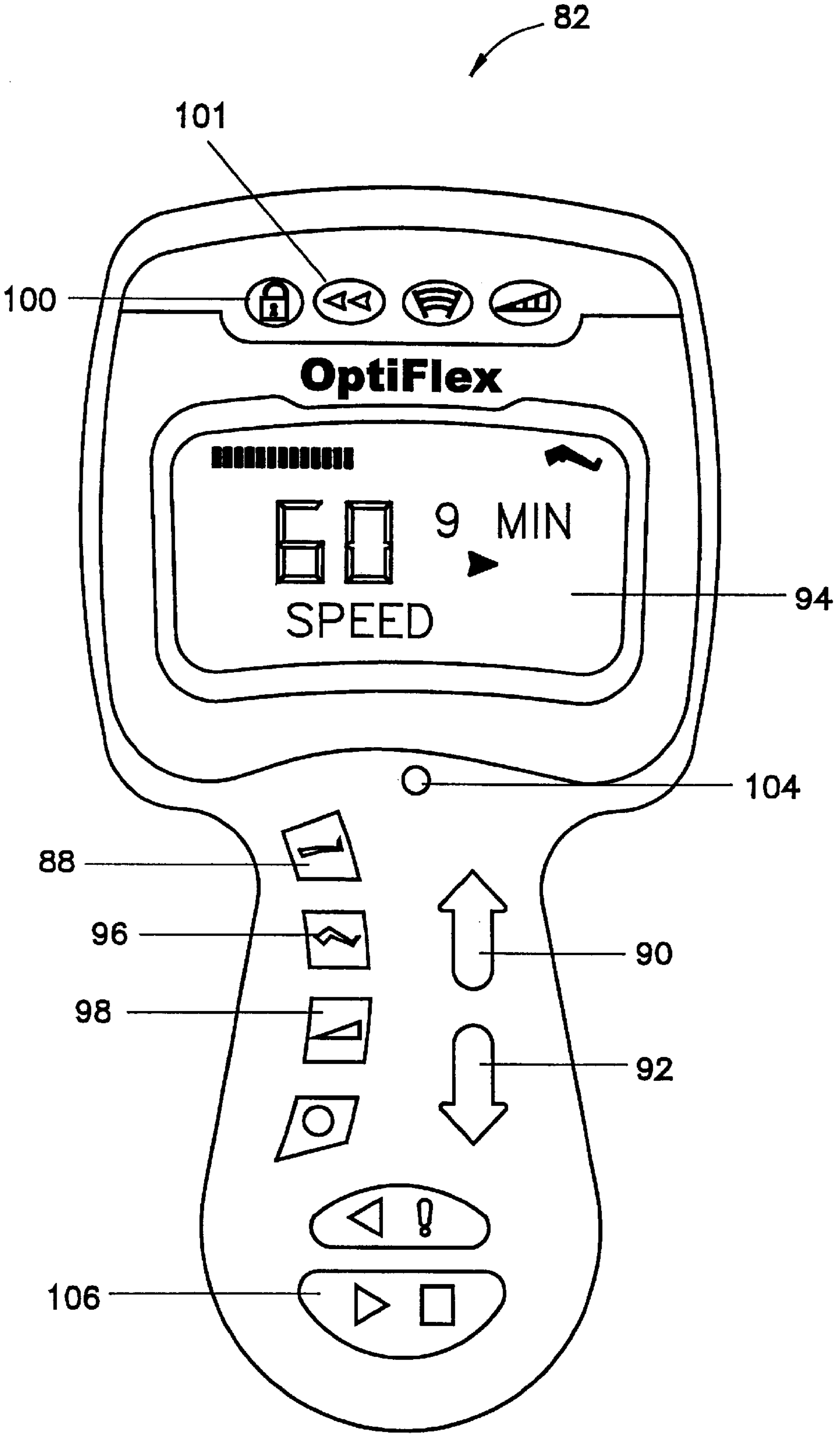
FIG. 6 is a front view of a control pendent that may be used in connection with the preferred embodiment of the invention.

In order to begin treatment using device 10, a power cord (not shown) is attached at power receptacle 84 (see FIG. 3) and connected to a common 110V electrical power circuit. On/Off switch 86 may then be then activated to energize the machine. Referring now to FIG. 6, the patient may set the extension limit of the operational range of motion by pressing Extension button 88 while pressing the Up button 90 or the Down button 92. Once the Extension button is pressed, the currently programmed extension limit (expressed as an extension angle) will appear on LCD display 94, along with an appropriate notation such as "Extension Angle". The display will also show the changes in the extension angle while both the Extension button 88 and either the Up or Down buttons are pressed. Once the desired extension limit for the operational range of motion is set, the operational flexion limit and the first rate or speed of pivoting operation may be set by the same method using the Flexion button 96 along with the Up and Down buttons, and the Speed button 98 and the Up and Down buttons.

The Fast Back feature of the invention may then be activated by pressing both the Mode button 100 and the Fast Back button 101. An icon will appear on LCD display 94 to confirm the active status of the Fast Back feature. The display will also show the currently programmed flexion limit (expressed as a flexion angle, in degrees). An alphanumeric prompt will also appear on display 94 for the patient or therapist to set the intermediate flexion angle. The user will then press Flexion button 96, while simultaneously pressing Up button 90 or Down button 92 to establish the desired intermediate flexion angle. The display will reflect these changes. As soon as the user presses Flexion button 96, an alphanumeric prompt such as "Press Mode to Accept Final Intermediate Flex Angle" will appear. Once the desired angle is reached, as indicated by the display, the user may set the intermediate flexion angle by pressing Mode button 100. If it is necessary at any time to clear the current setting, the Reset button 104 may be pressed. The same process will be repeated if it is desired to set an intermediate extension angle. If it is not desired to set an intermediate extension angle, the patient or therapist may simply press the Mode button 100 again. Once the Fast Back feature has been activated and the operational range of motion limits and intermediate angles have been set, an alphanumeric prompt will appear on the display 94 for the patient or therapist to set the rate at which the driver will move through the working range of motion.

In the preferred embodiment, the patient or therapist need only set the operational range of motion limits, a first rate of pivoting operation and activate the Fast Back feature of the invention. Once the Fast Back feature is activated, the controller will establish default values for the critical flexion angle and second rate of pivoting operation. The preferred default value for the critical flexion angle is approximately 10° greater than the operational flexion angle. The preferred default value for the second rate of pivoting operation is the lesser of fifty percent of the first rate of pivoting operation or 75° per minute. The patient or therapist need only press the Start/Stop button 106 to set the device 10 into motion, unless he desires to override the default limits, in which case he may input data in the same manner described above.

Once the Fast Back feature is activated, the motor will drive the driver along the axis of the frame, back and forth in a substantially continuous fashion, so as to move the patient's leg through a plurality of cycles of motion, each of which imposes a range of motion on the patient's leg comprising a flexion phase and an extension phase. The direction of movement of the driver along the axis of the frame will reverse when the driver reaches an operational flexion limit or an operational extension limit. Preferably, the device will accommodate a flexion limit corresponding to a flexion angle $\theta_f$ of about 60° or greater, and an extension limit corresponding to an extension angle $\theta_e$ of about 190° or less. The invention also contemplates that display 94 may express any of the flexion and/or extension angles referred to herein as 180°−θ. In other words, a flexion angle $\theta_f$ of 60° may be expressed as 120° (180°−60°), and an extension angle $\theta_e$ of 190° may be expressed as −10° (180°−190°).

In the preferred embodiment of the invention, the means (comprised of the combination of controller 77 and control pendant 82) for setting the intermediate angle may be configured so as to set such angle to affect the rate of operation only during a flexion phase, consistent with the most common treatment regimen that is prescribed for knee rehabilitation. For other treatment regimens, however, it may be appropriate to configure the machine to set such angle to affect the rate of operation only during a extension phase.

As has been described above, the preferred embodiment further provides means (comprised of the combination of controller 77 and control pendant 82) for selecting a first rate at which the driver will move along the axis to pivot the upper leg support and the lower leg support between the operational extension limit and the intermediate flexion limit during the flexion phase and between the operational flexion and operational extension limits during the extension phase, as well as means (comprised of the combination of controller 77 and control pendant 82) for selecting (or accepting by default) a second rate at which the driver will move along the axis to pivot the upper leg support and the lower leg support between the intermediate flexion limit and the operational flexion limit during the flexion phase.

The invention also includes means (comprised of the combination of controller 77 and control pendant 82) for changing the rate at which the driver moves along the axis of the frame to pivot the upper leg support and the lower leg support from the first rate to the second rate and from the second rate back to the first rate. In the preferred embodiment, control means (comprised of the combination of controller 77 and control pendant 82) are also provided for decelerating the driver from the first rate to the second rate at a predetermined rate as the driver approaches the intermediate angle. A trigger angle is set at a point along the axis from the intermediate angle where it is desired that such deceleration begin. This trigger angle is the angle between the upper leg support and the lower leg support. If the intermediate angle is set as a flexion angle, the trigger angle is preferably 5° greater than the critical flexion angle (or approximately 15° greater than the operational flexion angle). If the intermediate angle is set as an extension angle, the trigger angle is preferably 5° less than the critical extension angle (or approximately 15° less than the operational extension angle). In the preferred embodiment, once the device is operating and the Fast Back feature has been activated and a first rate, a second rate and a critical flexion angle have been set, the driver will begin moving along the axis of the frame at the first rate from the programmed operational extension limit towards the operational flexion limit. When the driver reaches a point along the axis of the frame at the first rate which corresponds to a trigger angle which is approximately 5° greater than the critical flexion angle, it will begin to decelerate. The rate of deceleration is preferably constant, but may be adjusted, if desired. Preferably, the driver will decelerate from the first rate at the trigger angle to a second rate which is equal to the lesser of 50% of the first rate or 75° per minute at the intermediate flexion angle. The driver will continue to move along the axis to the operational flexion limit, at the second rate, whereupon the driver will reverse direction and move towards the operational extension limit at the first rate of operation. When the driver reaches the point along the axis which corresponds with the operational extension limit, the driver will reverse direction and will again move towards the intermediate flexion angle at the first rate of operation.

The preferred embodiment of the invention also contemplates a Soft Turns feature by which sudden changes in speed and direction at the flexion and extension limits are avoided. According to this embodiment of the invention, control means (comprised of the combination of controller 77 and control pendant 82) are provided for decelerating the driver from the preset speed of motion at a predetermined rate as it approaches an extension limit (where the driver stops and changes direction) beginning at a predetermined distance along the axis from the extension limit. Control means (comprised of the combination of controller 77 and control pendant 82) are also provided for accelerating the driver from a stop at an extension limit to the preset speed of motion at a predetermined rate for a predetermined distance after the driver reverses direction upon reaching the extension limit. In addition, this embodiment of the invention includes control means (comprised of the combination of controller 77 and control pendant 82) for decelerating the driver from the preset speed of motion at a predetermined rate as it approaches a flexion limit (where the driver stops and changes direction) beginning at a predetermined distance along the axis from the flexion limit and control means (comprised of the combination of controller 77 and control pendant 82) for accelerating the driver from a stop at a flexion limit to the preset speed of motion at a predetermined rate for a predetermined distance after the driver reverses direction upon reaching the flexion limit. Preferably, the predetermined distance along the axis at which deceleration of the driver as it approaches an extension limit begins defines a point along the axis of the frame that establishes an angle between the upper leg support and the lower leg support that is approximately 1–2° less than the extension angle for such cycle. Furthermore, it is also preferred that the predetermined distance along the axis during which the driver is accelerated after it reverses direction upon reaching an extension limit defines a point along the axis of the frame that establishes an angle between the upper leg support and the lower leg support that is approximately 1–2° less than the extension angle for such cycle, and the predetermined distance along the axis at which deceleration of the driver as it approaches a flexion limit begins defines a point along the axis of the frame that establishes an angle between the upper leg support and the lower leg support that is approximately 1–2° greater than the flexion angle for such cycle. Furthermore, it is also preferred that the predetermined distance along the axis during which the driver is accelerated after it reverses direction upon reaching a flexion limit defines a point along the axis of the frame that establishes an angle between the upper leg support and the lower leg support that is approximately 1–2° greater than the flexion angle for such cycle. Finally, it is also preferred that the rate of deceleration and acceleration be constant.

As an example of operation of the Soft Turns and Fast Back features according to the preferred embodiment of the invention, an operational flexion limit may be set corresponding to a flexion angle of 80° and an operational extension limit may be set corresponding to an extension angle of 170°. An intermediate flexion angle is set at 90°. A trigger angle is set at 95°. The first speed of operation of the driver is set at 60° per minute, and the second speed is set at 30° per minute (the lesser of 50% of the first rate or 75° per minute). The points along the axis of the frame at which the Soft Turns acceleration and Soft Turns deceleration begin and end are set corresponding to angles between the upper and lower leg supports of 82° and 168°. When the driver is set in motion, it will move along the axis of the machine during the flexion phase at a rate of 60° per minute until it reaches a point corresponding to a flexion angle of 95°. At this point, the driver will begin decelerating from a speed of 60° per minute (the first rate) to a second rate of 30° per minute (one-half of the first rate). This deceleration will occur as the driver moves along the axis to the intermediate angle a point along the axis which corresponds with angle of 90°, the driver will be moving at the second rate of 30° per minute. The driver will continue to move along the axis of the machine during the flexion phase at the rate of 30° per minute until it reaches a point corresponding to a flexion angle of 82°. At this point, the driver will decelerate from a speed of 30° per minute to zero at the flexion limit (corresponding to an angle of 80°). Then it will accelerate as it moves from the flexion limit in the opposite direction. This acceleration will continue until the driver reaches a point corresponding to an extension angle of 82°, at which point the driver will be moving at the first speed of 60° per minute. The driver will maintain this speed (60° per minute) until it reaches a point corresponding to an extension angle of 168°. At this point, the driver will decelerate from a speed of 60° per minute to zero at the extension limit. Then it will change directions and accelerate as it moves from the extension limit. This acceleration will continue until the driver reaches a point corresponding to a flexion angle of 168°, at which point the driver will be moving at the first speed of 60° per minute.

The therapeutic device may also include a storage means 108 capable of storing data about one or more different patients including the extension and flexion limits used during a treatment session for each of the patients. The invention may also include a retrieval means by which the data in the storage means can be accessed at a later time.

Once the control after storage and data storage of the invention are appreciated, the controller 77 and data storage means 108 required for operating device 10 may be programmed by those having ordinary skill in the art to which the invention relates.

As can be seen from the description herein, the invention provides for the establishment of operational limits to the range of motion and intermediate angles through which it is desired that the patient's knee be flexed and his leg extended, whereby the rate of operation may be adjusted one or more times per cycle so that the device operates at a first rate which is more conducive to rehabilitation in the working or critical range of motion, and at a second rate in the non-working or non-critical range of motion which enables the carriage to return to the working range of motion more frequently than conventional one speed CPM machines, thereby increasing the amount of time the patient's knee spends in the working range of motion. Another advantage of a preferred embodiment of the invention is its Soft Turns capability, wherein the carriage holding the patient's leg is decelerated, at a controlled rate over a controlled distance, from the operational speed to zero, as the carriage approaches the extension or flexion limit, and wherein the carriage is accelerated in the same fashion as the carriage moves away from the extension or flexion limit.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A therapeutic device for use in providing physical therapy for a patient's knee, which device comprises:

(a) an elongated frame having an axis;

(b) a lower leg support having a first end and a second end and being adapted to support the lower leg of the patient;

(c) an upper leg support having a first end and a second end and being adapted to support the upper leg of the patient;

wherein the first end of the upper leg support is pivotally connected to the first end of the lower leg support so that said upper leg support and said lower leg support pivot with respect to each other through a plurality of pivotal positions, each of which establishes an angle between said upper leg support and said lower leg support; and wherein said frame, lower leg support and upper leg support are interconnected in a manner such that both the tibia and the femur of the patient are generally coplanar with the axis of the frame;

said therapeutic device further including:

(d) means for repeatedly pivoting the lower leg support and the upper leg support at the connection therebetween so as to move the patient's leg through a plurality of cycles of motion, each of which:

(1) imposes a range of motion on the patient's leg comprising a flexion phase, in which the angles of the pivotal positions between the lower leg support and the upper leg support are decreasing, and an extension phase, in which the angles of the pivotal positions between the lower leg support and the upper leg support are increasing;

(2) is defined by a flexion limit which establishes the minimum angle between the lower leg support and the upper leg support to which the lower leg support and the upper leg support are pivoted during a flexion phase and an extension limit which establishes the maximum angle between the lower leg support and the upper leg support to which the lower leg support and the upper leg support are pivoted during an extension phase;

(e) means for setting a desired range of motion including:

(1) an operational extension limit which corresponds to an operational extension angle between the upper leg support and the lower leg support to which the upper and lower leg supports are pivoted during the extension phase of a cycle; and (2) an operational flexion limit which corresponds to an operational flexion angle between the upper leg support and the lower leg support to which the upper and lower leg supports are pivoted during the flexion phase of a cycle;

(f) means for setting at least one intermediate angle within the desired range of motion, which corresponds to a critical angle between the upper leg support and the lower leg support, wherein each such intermediate angle:

(1) will correspond to a critical extension angle between the upper leg support and the lower leg support which is less than the operational extension angle; or (2) will correspond to a critical flexion angle between the upper leg support and the lower leg support which is greater than the operational flexion angle; and (g) means for setting a first rate at which the lower leg support and the upper leg support are pivoted at the connection therebetween;

(h) means for setting a second rate at which the lower leg support and the upper leg support are pivoted at the connection therebetween;

(i) means for changing the rate at which the lower leg support and the upper leg support are pivoted at the connection therebetween from the first rate to the second rate at the intermediate angle:

(1) during the extension phase if the intermediate angle is a critical extension angle; or (2) during the flexion phase if the intermediate angle is a critical flexion angle;

(j) means for changing the rate at which the lower leg support and the upper leg support are pivoted at the connection therebetween from the second rate to the first rate:

(1) at the operational extension limit if the rate is changed from the first rate to the second rate during the extension phase; or (2) at the operational flexion limit if the rate is changed from the first rate to the second rate during the flexion phase.

2. The device of claim 1 wherein the length of the lower leg support is adjustable.

3. The device of claim 1 wherein the second rate is set at the lesser of 50% of the first rate or 75° per minute.

4. The device of claim 1 which includes:

(a) means for setting at least one trigger angle between the upper leg support and the lower leg support within the desired range of motion, wherein each such trigger angle is set:

(1) as an angle which is less than the operational extension angle and greater than the critical angle, if the intermediate angle was set as a critical extension angle; or (2) as an angle which is greater than the operational flexion angle and less than the critical angle, if the intermediate angle was set as a critical flexion angle;

(b) means for decelerating the rate at which the lower leg support and the upper leg support are pivoted at the connection therebetween from the first rate at the trigger angle to the second rate at the intermediate angle.

5. The device of claim 4 wherein the trigger angle is approximately:

(a) 5° less than the critical extension angle if the intermediate angle is an extension angle; or (b) 5° greater than the critical flexion angle if the intermediate angle is a flexion angle.

6. The device of claim 1:

(a) wherein the upper leg support includes:

(1) an upper portion; and (2) a third support having a first end and a second end, the first end being pivotally attached to the frame and the second end being pivotally attached to the lower leg support; and (3) a linkage having a first end and a second end, the first end being pivotally attached to the upper portion and the second end being pivotally attached to the third support;

(b) wherein the means for repeatedly pivoting the lower leg support and the upper leg support at the connection therebetween includes:

(1) a motor;

(2) a driver that is adapted to move in both directions along the axis of the frame; and (3) a drive means that is adapted to interconnect the motor and the driver so that operation of the motor will move the driver along the axis of the frame;

(c) wherein the second end of the lower leg support is attached to the driver;

wherein the upper leg support, the lower leg support, the third support and the linkage are arranged and interconnected so that the upper leg support may pivot about a virtual pivot axis which is proximate to the patient's hip joint; and wherein because of the interconnection of said supports and the linkage, and the connection of the lower leg support to the driver, movement of the driver in one direction along the axis comprises an extension phase and movement of the driver in the opposite direction along the axis comprises a flexion phase;

(d) which device includes:

(1) a foot support which is mounted to the lower leg support at its second end;

(2) means for setting a desired range of motion including an operational extension limit which corresponds to a point along the axis of the frame to which the driver is moved during the extension phase by operation of the motor to establish an operational extension angle between the upper leg support and the lower leg support, and an operational flexion limit which corresponds to a point along the axis of the frame to which the driver is moved by operation of the motor during the flexion phase to establish an operational flexion angle between the upper leg support and the lower leg support;

(3) means for setting at least one intermediate point along the axis of the frame to which the driver is moved by operation of the motor to establish a critical angle between the upper leg support and the lower leg support, wherein each such point:

(i) establishes a critical extension angle which is less than the operational extension angle; or (ii) establishes a critical flexion angle which is greater than the operational flexion angle;

(4) means for setting a first rate at which the driver will move along the axis to pivot the upper leg support and the lower leg support;

(5) means for setting a second rate at which the driver will move along the axis to pivot the upper leg support and the lower leg support;

(6) means for changing the rate at which the driver moves along the axis from the first rate to the second rate at the intermediate point:

(i) during the extension phase if the intermediate point corresponds to a critical extension angle; or (ii) during the flexion phase if the intermediate point corresponds to a critical flexion angle;

(7) means for changing the rate at which the driver moves along the axis from the second rate to the first rate:

(i) at the operational extension limit if the rate is changed from the first rate to the second rate during the extension phase; or (ii) at the operational flexion limit if the rate is changed from the first rate to the second rate during the flexion phase;

(8) means for activating the motor to drive the driver along the axis of the frame;

(9) means for reversing the direction the driver moves along the axis of the frame during a flexion phase when the driver reaches an operational flexion limit;

(10) means for reversing the direction the driver moves along the axis of the frame during an extension phase when the driver reaches an operational extension limit.

7. The device of claim 6 wherein the length of the third support is adjustable.

8. The device of claim 6 wherein the foot support is pivotally mounted at the second end of the lower leg support.

9. The device of claim 6 wherein:

(a) the drive means includes an externally threaded drive rod which is mounted in the frame and disposed along the axis of the frame, which drive rod is adapted to be turned by the motor; and (b) the driver includes an internally threaded nut that is adapted to mate with the drive rod, which nut is mounted on the drive rod in threaded engagement therewith, so that the driver moves along the axis of the frame as the drive rod is turned by the motor.

10. The device of claim 6 which includes:

(a) means for decelerating the driver at a predetermined rate as it approaches an extension limit beginning at a point located a predetermined distance along the axis from the extension limit;

(b) means for accelerating the driver at a predetermined rate for a predetermined distance after it reverses direction upon reaching an extension limit;

(c) means for decelerating the driver at a predetermined rate as it approaches a flexion limit beginning at a point located a predetermined distance along the axis from the flexion limit; and (d) means for accelerating the driver at a predetermined rate for a predetermined distance after it reverses direction upon reaching a flexion limit.

11. The device of claim 10 wherein:

(a) the point located a predetermined distance along the axis from the extension limit at which deceleration of the driver begins as the driver approaches an extension limit establishes an angle between the upper leg support and the lower leg support that is approximately 1–2° less than the angle of the extension limit for such cycle;

(b) the predetermined distance along the axis during which the driver is accelerated after it reverses direction upon reaching an extension limit defines a point along the axis of the frame that establishes an angle between the upper leg support and the lower leg support that is approximately 1–2° less than the angle of the extension limit for such cycle;

(c) the point located a predetermined distance along the axis from the flexion limit at which deceleration of the driver begins as the driver approaches a flexion limit establishes an angle between the upper leg support and the lower leg support that is approximately 1–2° greater than the angle of the flexion limit for such cycle; and (d) the predetermined distance along the axis during which the driver is accelerated after it reverses direction upon reaching a flexion limit defines a point along the axis of the frame that establishes an angle between the upper leg support and the lower leg support that is approximately 1–2° greater than the angle of the flexion limit for such cycle.

12. The device of claim 6 which includes a storage means capable of storing data about one or more patients including the extension and flexion limits used during a treatment session for each of the patients.

13. The device of claim 6 wherein the second rate at which the driver moves along the axis is fifty percent of the first rate at which the driver moves along the axis.

14. The device of claim 6 which includes means for decelerating the driver from the first rate to the second rate at a predetermined rate as it approaches:

(a) the intermediate point corresponding to a critical extension angle, from the flexion limit beginning at a point located a predetermined distance along the axis from the intermediate point; or (b) the intermediate point corresponding to a critical flexion angle, from the extension limit beginning at a point located a predetermined distance along the axis from the intermediate point.

15. The device of claim 14 wherein the point located a predetermined distance along the axis from the intermediate point at which deceleration of the driver begins as the driver approaches the intermediate point establishes a trigger angle between the upper leg support and the lower leg support that is approximately:

(a) 5° less than the critical extension angle; or (b) 5° greater than the critical flexion angle.

16. A method of providing physical therapy for a patient's knee by moving the patient's leg through a plurality of cycles of motion in which the patient's upper leg is pivoted with respect to the patient's lower leg at the knee, wherein each cycle imposes a range of motion on the patient's leg comprising a flexion phase in which the angle between the femur of the patient's upper leg and the tibia of the patient's lower leg is decreasing and an extension phase in which the angle between the femur of the patient's upper leg and the tibia of the patient's lower leg is increasing, and wherein each cycle of motion is defined by a flexion limit which establishes the minimum angle between the femur of the patient's upper leg and the tibia of the patient's lower leg to which the patient's leg is pivoted during a flexion phase and an extension limit which establishes the maximum angle between the femur of the patient's upper leg and the tibia of the patient's lower leg to which the patient's leg is pivoted during an extension phase, which method comprises:

(a) providing a therapeutic device that is adapted to receive the upper leg and the lower leg of a patient, said device comprising:

(1) an elongated frame having an axis;

(2) a motor;

(3) a driver that is adapted to move in both directions along the axis of the frame; and (4) a drive means that is adapted to interconnect the motor and the driver so that operation of the motor will move the driver along the axis of the frame;

(5) a lower leg support having a first end and a second end and being adapted to support the lower leg of the patient, wherein the second end of the lower leg support is attached to the driver;

(6) an upper leg support having a first end and a second end and being adapted to support the upper leg of the patient, wherein the first end of the upper leg support is pivotally connected to the first end of the lower leg support and wherein the upper leg support includes:

(A) an upper portion; and (B) a third support having a first end and a second end, the first end being pivotally attached to the frame and the second end being pivotally attached to the lower leg support; and (C) a linkage having a first end and a second end, the first end being pivotally attached to the upper portion and the second end being pivotally attached to the third support;

wherein the upper leg support, the lower leg support, the third support and the linkage are arranged and interconnected so that the upper leg support pivots about a virtual pivot axis which is proximate to the patient's hip joint; and wherein because of the interconnection of said supports and the linkage, and the connection of the lower leg support to the driver, movement of the driver in one direction along the axis comprises an extension phase and movement of the driver in the opposite direction along the axis comprises a flexion phase, so that movement of the driver along the axis of the frame will cause said upper leg support and said lower leg support to be pivoted with respect to each other through a plurality of pivotal positions, each of which establishes an angle between said upper leg support and said lower leg support corresponding to an angle between the femur of the patients upper leg and the tibia of the patient's lower leg;

(7) a foot support which is mounted to the lower leg support at its second end;

(8) means for setting a desired range of motion including an operational extension limit which corresponds to a point along the axis of the frame to which the driver is moved during the extension phase of a cycle by operation of the motor to establish an operational extension angle between the upper leg support and the lower leg support, and an operational flexion limit which corresponds to a point along the axis of the frame to which the driver is moved by operation of the motor during the flexion phase of a cycle to establish an operational flexion angle between the upper leg support and the lower leg support;

(9) means for setting at least one intermediate point along the axis of the frame to which the driver is moved by operation of the motor to establish a critical flexion angle between the upper leg support and the lower leg support which is greater than the operational flexion angle;

(10) means for setting a first rate at which the driver will move along the axis to pivot the upper leg support and the lower leg support;

(11) means for setting a second rate at which the driver will move along the axis to pivot the upper leg support and the lower leg support;

(12) means for changing the rate at which the driver moves along the axis during the flexion phase from the first rate to the second rate at the intermediate point;

(13) means for changing the rate at which the driver moves along the axis from the second rate to the first rate at the operational flexion limit;

(14) means for activating the motor to drive the driver along the axis of the frame;

(15) means for reversing the direction the driver moves along the axis of the frame during a flexion phase when the driver reaches an operational flexion limit;

(16) means for reversing the direction the driver moves along the axis of the frame during an extension phase when the driver reaches an operational extension limit;

(b) setting an operational extension limit;

(c) setting an operational flexion limit;

(d) setting an intermediate point;

(e) setting a first rate at which the driver is moved along the axis;

(f) setting a second rate at which the driver is moved along the axis;

(g) activating the motor to move the driver along the axis of the frame by operation of the motor;

(h) moving the driver at the first rate from the operational extension limit to the intermediate point;

(i) changing the rate at which the driver moves along the axis from the first rate to the second rate;

(j) moving the driver at the second rate from the intermediate point to the operational flexion limit;

(k) changing the direction of movement of the driver along the axis of the frame at the operational flexion limit;

(l) changing the rate at which the driver moves along the axis from the second rate to the first rate;

(m) moving the driver at the first rate from the operational flexion limit to the operational extension limit;

(n) changing the direction of movement of the driver along the axis of the frame at the operational extension limit.

17. The method of claim 16 wherein the second rate at which the driver moves along the axis of the frame is the lesser of fifty percent of the first rate or 75° per minute.

18. The method of claim 16 which includes decelerating the driver from the first rate to the second rate at a predetermined rate as it approaches the intermediate point beginning at a point located a predetermined distance along the axis from the intermediate point.

19. The method of claim 18 wherein the point located a predetermined distance along the axis from the intermediate point at which deceleration of the driver begins as the driver approaches the intermediate point establishes a trigger angle between the upper leg support and the lower leg support that is approximately 5° greater than the angle of the intermediate point.

* * * * *